(12) United States Patent
Valjakka et al.

(10) Patent No.: US 7,596,400 B2
(45) Date of Patent: Sep. 29, 2009

(54) ELECTRODE DETECTOR FOR MONITORING BIOPOTENTIAL ON TISSUE

(75) Inventors: Antti Valjakka, Saunarannantie 27, FIN-71570 Syvänniemi (FI); Arto Urtti, Kuopio (FI); Janne Ahonen, Kuopio (FI)

(73) Assignee: Antti Valjakka, Syvanniemi (FI)

( * ) Notice: Subject to any disclaimer, the term of this patent is extended or adjusted under 35 U.S.C. 154(b) by 0 days.

(21) Appl. No.: 10/974,865

(22) Filed: Oct. 26, 2004

(65) Prior Publication Data

US 2005/0119544 A1 Jun. 2, 2005

Related U.S. Application Data

(63) Continuation of application No. PCT/FI03/00352, filed on May 5, 2003.

(30) Foreign Application Priority Data

May 6, 2002 (FI) .................................. 20020850

(51) Int. Cl.
*A61B 5/00* (2006.01)
*A61B 5/04* (2006.01)
*A61B 5/0496* (2006.01)
(52) U.S. Cl. ...................... 600/383; 600/558
(58) Field of Classification Search ................ 600/383, 600/372, 558
See application file for complete search history.

(56) References Cited

U.S. PATENT DOCUMENTS 4,131,113 A 12/1978 Fender et al. ............... 600/558

(Continued)

FOREIGN PATENT DOCUMENTS

FR 2 713 913 A1 6/1995

(Continued)

OTHER PUBLICATIONS

Hawlina, M. et al., "HK-Loop Ag Fibre Electrode for Clinical Eletroretinography", 1992, Documenta Ophthalmalogica 81, pp. 252-259.

(Continued)

*Primary Examiner*—Lee S Cohen
(74) *Attorney, Agent, or Firm*—Harrington & Smith, PC

(57) ABSTRACT

The present invention relates to an electrode detector, which comprises a contact electrode part adjustable to tissue, or being in touch with it and which contact electrode part is for monitoring biopotential or other physical magnitude, a conducting wire (2) attached to the contact electrode part, electroconductive material, non-electroconductive material and electronics processing the signal. The electrode detector in accordance with the invention comprises a ball-shaped or almost ball-shaped contact electrode part, monitoring biopotential or some other physical magnitude, the covering part of which contact electrode part is made of non-toxic material to tissue and some electroconductive part of which has been galvanically or capacitively or indirectly through an electronic circuitry in the contact electrode part itself connected to the electroconductive inner part of a flexible conducting wire while its covering part is made of material that is non-toxic to tissue and insulating electricity, and attaching part of which has been connected or may be connected galvanically, non-galvanically or indirectly through the electronic circuitry in the attaching part to the conducting wire of the electrode detector and which may be anchored with external attaching elements/attaching material in it or some other external attaching elements/materials near the subject to be monitored.

6 Claims, 3 Drawing Sheets

U.S. PATENT DOCUMENTS

| | | | |
|---|---|---|---|
| 4,417,581 A | 11/1983 | Dawson | 600/383 |
| 4,735,207 A | 4/1988 | Nambu et al. | 128/639 |
| 4,874,237 A | 10/1989 | Cringle | 221/221 |
| 5,154,174 A | 10/1992 | Hawlina | 128/639 |
| 5,297,554 A | 3/1994 | Glynn et al. | 600/476 |
| 5,303,703 A * | 4/1994 | Monti-Bloch | 600/383 |
| 5,506,633 A | 4/1996 | Sperling | 351/206 |
| 6,208,882 B1 | 3/2001 | Lenarz et al. | 600/379 |

FOREIGN PATENT DOCUMENTS

| | | |
|---|---|---|
| SU | 1648336 A1 | 5/1991 |
| WO | WO 00/40146 | 7/2000 |

OTHER PUBLICATIONS

Bayer, A. et al., "Comparisons of the Amplitude Size and the Reproducibility of Three Different Electrodes to Record the Corneal Flash Electroretinogram in Rodents", 2000, Documenta Ophthalmalogica 98, pp. 233-246.

* cited by examiner

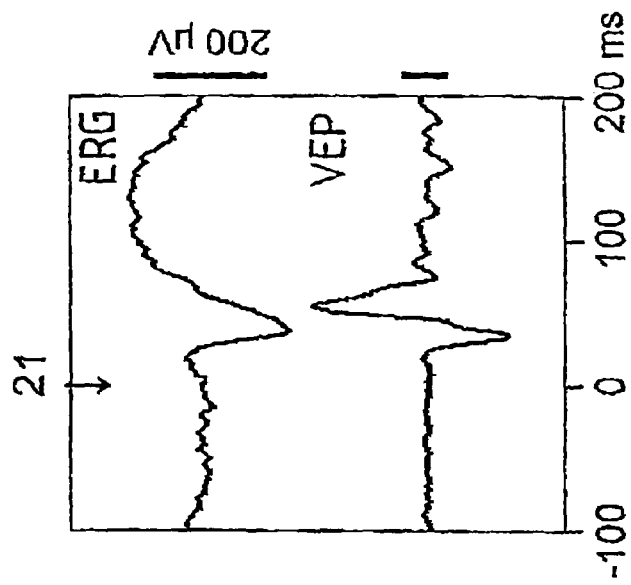
FIG. 3C
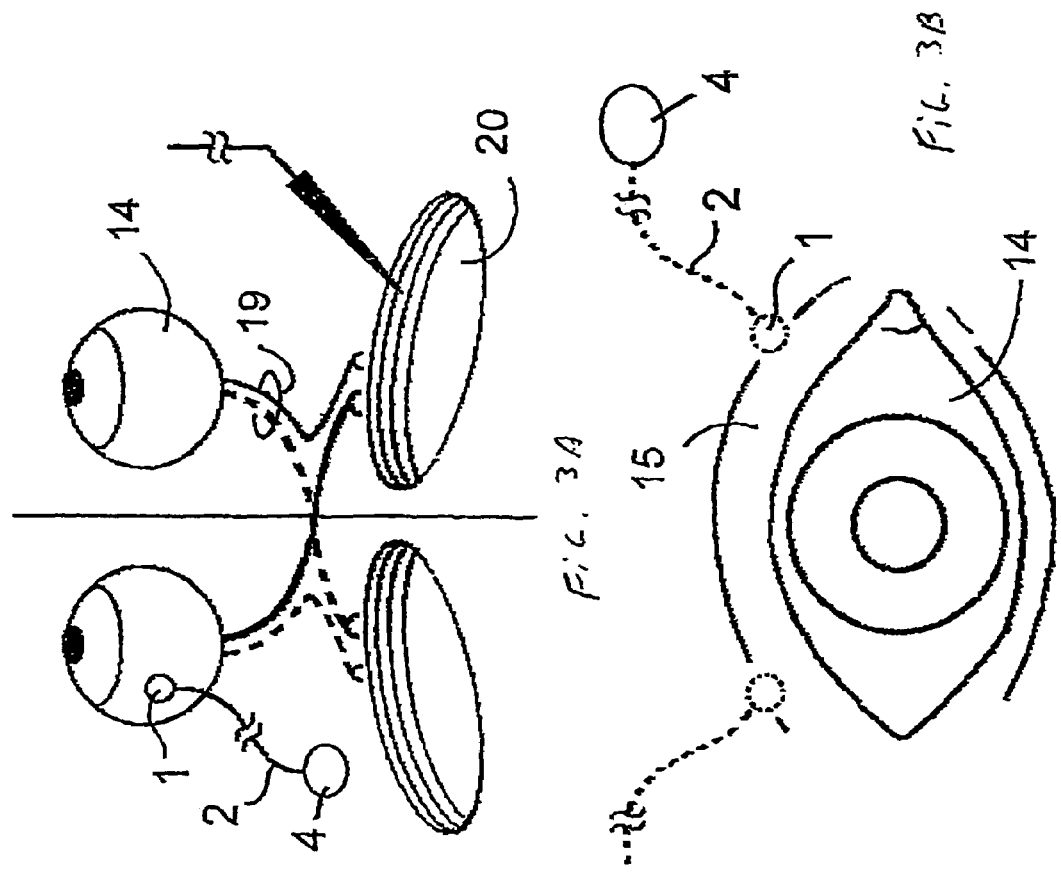
FIG. 3A
FIG. 3B

ELECTRODE DETECTOR FOR MONITORING BIOPOTENTIAL ON TISSUE

CROSS REFERENCE TO RELATED APPLICATION

This application is a continuation of International Patent Application No. PCT/FI03/00352 filed May 5, 2003.

The present invention relates to an electrode detector, which includes a contact electrode part for monitoring biopotential or other physical magnitude of the tissue, a conducting wire attached to the contact electrode part, material conducting electricity, material not conducting electricity and electronics for processing the signals.

BACKGROUND OF THE INVENTION

In visual measurement methods based on a recognized technique which methods have been designed for measuring the physiological potential difference in the retina of the eye (ERG, electroretinogram) for visual stimulus on test animals the electrode types referred to and to be adjusted in the eye and which electrodes registrate the ERG response have been constructed such that the use of those requires anaesthesia or immobility of the test animal such that the contact part of the electrodes measuring the biopotential is well kept on place and that they could in such way measure ERG responses of the same size and without interference. For example, the thread electrode, the cotton wick-Ag/AgCl-electrode and a contact lens with golden coat-electrode described in publication Documenta Ophthalmologica 98: 2000, Bayer A. U., Mittag T., Cook P., Brodie S. E., Podos S. M. and Maag K-P. "Comparisons of the amplitude size and the reproducibility of three different electrodes to record the corneal flash electroretinogram in rodents", p. 233-246, and penlike pointer tip including a light source for stimulation of the retina and the electrode blades for measuring the ERG response described in SU-patent publication 1648336 are these kind of recognized electrode types adjustable on the cornea of the eye.

On the other hand, also other recognized electrodes which have been designed for measuring the ERG response on a human, but which, in some cases, may be applied for monitoring test animals are designed by shape such that their use requires the subject to be immovable during the measurements. Electrodes described in these methods are:

(1) A looplike, so called, HK-loop electrode for clinical ERG-measurements (Documenta Ophthalmologica 81:1992, Hawlina M. and Konec B. "New noncorneal HK-loop electrode for clinical electroretinography", p. 253-259; U.S. Pat. No. 5,154,174)
(2) A cluster of electrodes placed on the sclerotic membrane of eye, in which electrode cluster there are several separate contact blades of electrodes sank in a ringlike and concave insulation frame following the surface of the eye for use in clinical and experimental (that is for test animals) ERG measurements (U.S. Pat. No. 4,874,237).
(3) A contact lens kind of device placed on the corneal membrane of the eye for clinical monitoring of functioning of the cardiovascular system and ERG (U.S. Pat. No. 5,297,554).
(4) A nylon fibre electrode coated with silver and adjustable on the corneal membrane of the eye for clinical ERG registrations (U.S. Pat. No. 4,417,581).
(5) A thin, membrane-type, mold to desired form electrode including water to be attached on the corneal membrane for applying in clinical and experimental ERG measurements (U.S. Pat. No. 4,735,207).
(6) An electroretinografic transparent coat with taps holding the eyelids open to be adjusted on the corneal membrane for applying in clinical and experimental ERG measurements (FR patent publication 2713913).
(7) A metal strip to be attached on the skin, on the lower eyelid for example, which metal strip has been connected to a flexible plastic strip for measuring ERG and the outside cranium-reflected responses on a human (U.S. Pat. No. 4,255,023).
(8) A transparent cup electrode to be attached on the corneal membrane, on the edges of which cup electrode there is a metal ring for defining ERG on a human (U.S. Pat. No. 4,131,113).
(9) A metal wire to be attached on the lower eyelid on the skin for clinical ERG registrations (U.S. Pat. No. 5,506,633).

Most of these referred techniques enable the registration of ERG and other visual responses reflected outside the cranium on a conscious human, because a test person is able to stay immovable deliberately. Applying above mentioned techniques in monitoring test animals is difficult in that with registration of ERG on test animals under anaesthesia or made immovable the kind of drugs have to be used which change the functioning of cells of the central nerve system and thus the normal physiology of seeing.

The common limiting factor of recognized detectors designed for visual monitoring is their shape which may cause irritation changes in the eye or in the surrounding tissue or excessive stress on the eye if they were implanted permanently on the eye, for example under the eyelid. Secondly, a limiting factor, which excludes their permanent implantation in the eye is the fact that the electrode conductors have been described to be directed outwards from the eye where they have been presented to be connected to the actual measuring system. The third problem connected with recognized electrode detectors is the fact how the contact part measuring the biopotential and being connected to the tissue is kept on place while changing stresses are directed to it through the eye and the tissue around it. On the other hand, a problem connected with earlier mentioned is the fact that no stresses ought to be directed to the contact part of the electrode due to possible movements of the measuring wire.

The object of the invention is to eliminate these problems and to provide an electrode detector, which is (a) such by construction that the contact electrode part measuring the biopotential is fixed to hold on desired place, (b) the contact electrode part yields under mechanical stress directed to it and returns to its place by a little movement, (c) the electrode detector does not cause mechanical or chemical tissue injury and (d) mechanical stresses of the measuring wire which is possible to be connected to the electrode detector are not transmitted to the contact electrode part.

DESCRIPTION OF THE INVENTION

The electrode detector according to the invention comprises a ball-shaped contact electrode part monitoring biopotential or some other physical magnitude, the covering part of which contact electrode part is made of non-toxic material to tissue and some electroconductive part of which has been galvanically, or capacitively, or indirectly through an electronic circuitry in the contact electrode part itself, connected to the electroconductive inner part of a flexible conducting wire while its covering part is made of material that is non-toxic to tissue and isolates electricity, and the attaching part which has been connected or may be connected galvanically, or non-galvanically, or indirectly through the electronic circuitry in the attaching part, to the conducting wire of the electrode detector, and which attaching part may be anchored with external attaching elements/attaching material or attaching elements/material in it, near the object to be monitored.

The ball-kind of shape of the contact electrode part in accordance with the invention does not cause mechanical wearing injuries or irritation changes while placed in living biological tissue or while placed against such. The contact electrode part measuring biosignal keeps on place when the conducting wire penetrates a space which the contact electrode part and the attaching part do not penetrate and when the attaching part may be anchored on place with attaching elements. The ball shaped contact electrode part does not direct too much stress on the object to be measured, due to movements of the tissue, for example, because while connected to a flexible wire it yields. While the attaching part may be anchored with attaching elements in it or with external attaching parts the movements of the measuring wire connected to it are not transmitted to the contact electrode part and the signal processing with an electronic circuitry in the electrode detector itself minimizes the relative proportion of interference signals with respect to biosignal.

The earlier mentioned purposes, for measuring the ERG biopotential response, for example, are achieved by employing the ball-shaped contact electrode part in accordance with the invention which contact electrode part may be surgically implanted to a desired place in tissue, such as under the eyelid, against the sclerotic membrane or whatever suitable place in the eye or non-invasively externally on tissue to a suitable place. An electrode detector with earlier mentioned properties enables, among other things, evaluation of functioning of the eye and indirectly the optic nerve of eye of a freely moving and conscious test animal in measurements during various points of time, for example, during several months, without surgical operations in connection with these measurements. Naturally, in certain conditions, with these kinds of electrode detectors it is possible to measure the ERG in a human eye. An electrode detector meeting the earlier mentioned requirements may be applied as well in measurements of other physical magnitudes, such as temperature, conductibility, pressure in a monitored object while the measurement problem is as described in the introduction.

A contact electrode, the size of which depends on the subject to be measured, may be made of whatever material with good conductivity of electricity, preferably of pure precious metal. In cases, where electroconductive material is toxic to tissue it may be coated with electroconductive (pure silver, for example) or non-electroconductive material (Teflon-plastic, for example) which has no toxic influence on tissue. The biopotential change, caused by tissue and taken place in contact electrode part is transmitted to the electric wire attached to it, which is possible to place inside tissue while coated with insulation that is non-toxic to tissue, such as Teflon or similar.

A conducting wire has been attached or is connectable immovably to the attaching part, which may be anchored on place, near the object to be measured, by means of attaching elements on it and/or by means of external attaching elements/materials. The attaching part may be cast into plastic, for example, or similar material isolating electricity and being non-toxic to tissue. The attaching part may be anchored either inside tissue by means of bolts and hardening cold acrylic or externally by using a glue sticker or a suction cup. In cases when an electrode detector is planned to be placed against tissue, outside the body, the attaching part may be of flexible, gelatinous material (rubber, for example), which, in desired amount, surrounds the whole electrode detector. The attaching part may include electric connectors to the conducting wire of the contact electrode, to the wire to be connected to the registration system and to electronic component to be connected to it which electronic component processes the biosignal to be measured.

The electronic component may be, in that way, externally connectable with the attaching part. The electronic circuitry processing the signal may also be located inside the contact electrode part and/or attaching part. In an example, where a described electrode detector has been inserted in the eye of a test animal the contact electrode part of the electrode detector measuring the biopotential keeps on place in desired point of the eye such as between the eyelid and the conjunctiva/corneal membrane of the eye. This is realized by (a) the ability of the attaching part to be permanently anchored on place, (b) a conducting wire of the electrode detector with suitable bending strength and ability to return in shape after bending, (c) the location of the wire inside the tissue such that the tissue itself limits the movement sideways, (d) the location of the ball-kind of contact electrode part outside the tissue round a thin opening through the tissue where the conducting wire penetrates the tissue, and (e) forces of the eyelid and the conjunctiva or corneal membrane directed to the ball and limiting its movement. Because of these factors the contact electrode part of the electrode detector does not strain the surface of the eye with too strong stress although variable forces would be directed to the contact electrode part due to movements of the eye or tissue muscles because it yields while connected to a flexible conducting wire.

While the attaching part is possible to anchor permanently the movements of the measuring wire connected to it does not transmit stress on the ball-kind measuring electrode. This and the fact that the biosignal is possible to be processed (with a differential amplifier, for example) in the attaching part or in the contact electrode part themselves, enable the decreasing of interference signals with respect to the biosignal to be measured.

DESCRIPTION OF THE DRAWINGS

Next, the invention will be explained in more detail with reference to the accompanying drawings, in which.

FIG. 3A is a schematic view of the electrode detector shown in FIG. 1B at an eye of a subject and showing the optic nerve of the eye and the superior collilus of a subject;

FIG. 3B is a front view of an eye of a subject and the electrode detector shown in FIG. 1B; and FIG. 3C is a chart showing ERG and VEP measurements using the electrode detector shown in FIG. 1B.

In FIGS. 1 and 3 following numbers refer to various parts of the body: the eye 14, the eyelid 15, the sclerotic membrane of the eye 16, tissue 17, bone 18, the optic nerve of the eye 19, superior colliculus 20. Furthermore, in figures following numbers are used: a flashlight 21 and a light beam 22.

Figure 1A:
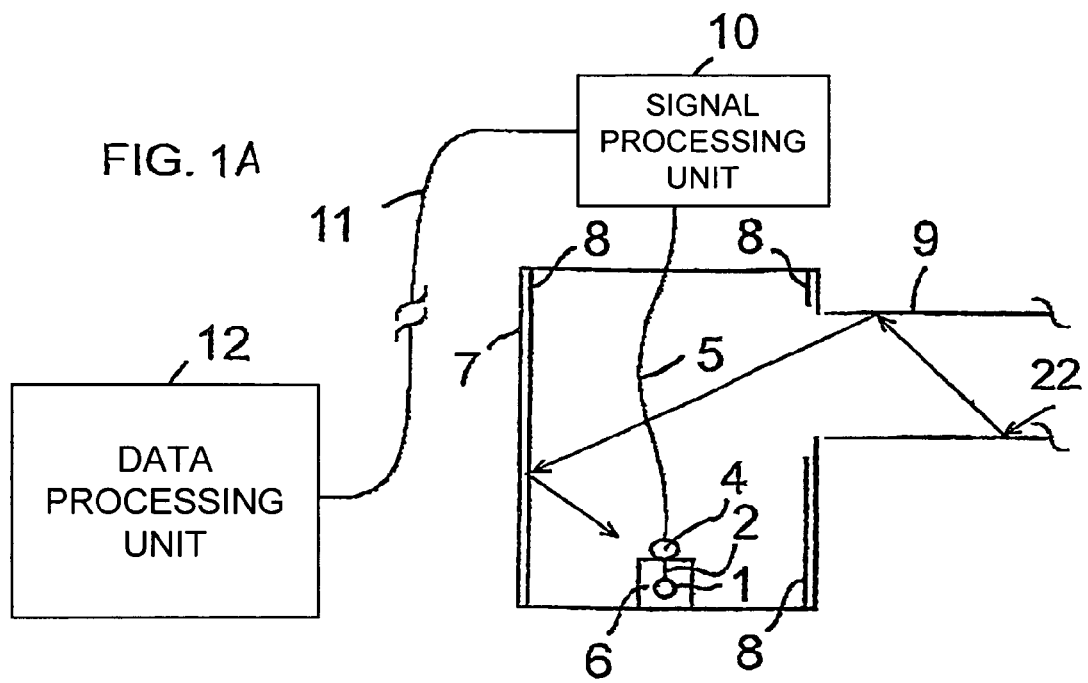
FIG. 1A illustrates a system comprising an electrode detector used in a chamber for measuring ERG response of an eye on a test animal.
Figure 1B:
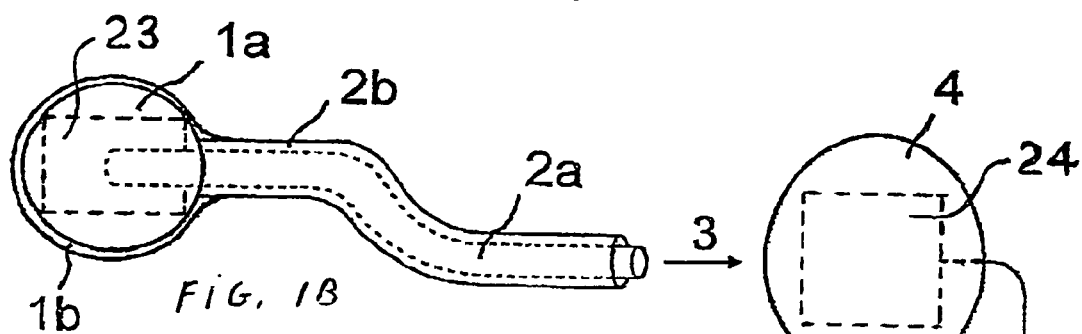
FIG. 1B is a diagram showing the electrode detector shown in FIG. 1A including a contact electrode part, a conducting wire, and an attaching part, wherein the conducting wire can be coupled to the attaching part by a coupling.
Figure 1C:
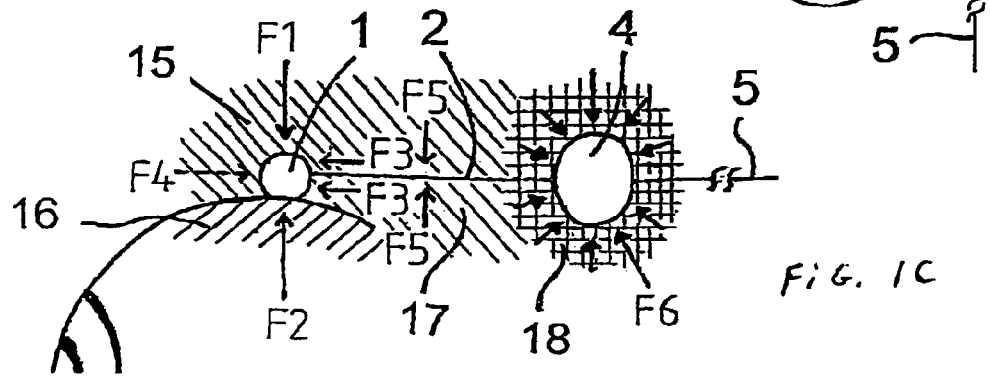
FIG. 1C illustrates forces directed by surrounding tissue to various sides of the electrode detector.
Figures 2A, 2B:
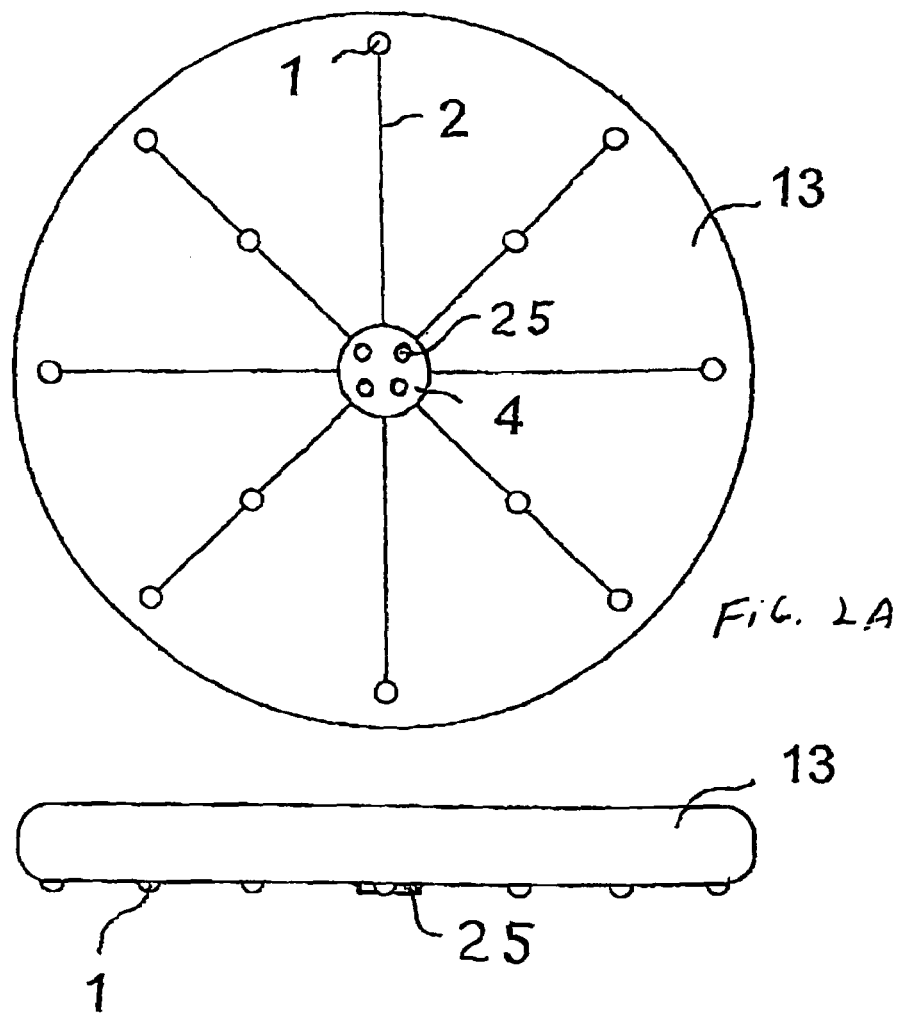
FIG. 2A is a top plan view of the electrode detector shown in FIG. 1B partially sunk in a gelatinous material.
FIG. 2B is a side view of the electrode detector and gelatinous material shown in FIG. 2A.

The electrode detector in figures 1A-C and 2A comprises a conducting wire 2, to one end of which a ball-shaped contact electrode part 1 has been connected. The contact electrode part 1 may be all over of same material such as pure silver, gold, carbon fibre or similar, which is advantageously electroconductive and non-toxic to tissue. On the other hand, the inner part 1a of the contact electrode part 1 may be made of whatever material and of one or several materials and of whatever shape, while being coated to a ball-shape with material, which is non-toxic to tissue. For example, while the covering part 1b is of glass, Teflon-plastic or similar, the inner part 1a may be of copper, tin, silver and so on solid and preferable high electroconductive material. In case the covering part 1b of the contact electrode part 1 is an electrical insulation it is preferably commonly continuous with the covering part 2b of the conducting wire 2 (Figure 1B). The area of the contact electrode part 2. may consist of areas bordered by each other and being made of various non-toxic materials, polyethylene polymers and silver, for example. The outer diameter of the contact electrode part 1 may measure 1.2 mm, for example, in ERG measurement on a rat. In the application in figure 2 there is a flexible gelatinous ring from where the ball-like, partly into gelatinous material 13 sunk, contact electrode parts 1 protrude. This kind of electrode detector may be placed against tissue in order to define its physical properties.

In an advantageous application of the invention some material of the inner part 1a of the contact electrode part 1 is in the liquid state. In the second advantageous application of the invention some material of the inner part 1a of the contact electrode part 1 is in the gaseous state. In the third advantageous application of the invention some part of the inner part 1a of the contact electrode part 1 is a vacuum, thus making the construction lighter.

The inner part 2a, conducting electricity, of the conducting wire 2 is preferably made of the same material as the material to which it is supposed to be connected in the contact electrode part 1, while a galvanic connection in question. The inner part 2a of the conducting wire 2 may be connected to the electroconductive material of the contact electrode part 1 galvanically, or capacitively, or indirectly through the electronic circuitry 23 processing the signal, which electronic circuitry 23 is placed in the contact electrode part. The inner part 2a of the conducting wire 2 is preferably a multistrand thread braiding in order to have a good mechanical strength. Some or all of the individual braidings may be coated with electrically insulating material. The electroconductive material of the inner part 2a of the conducting wire 2 as well as the electrically insulating material of the covering part 2b are preferably of material returning to its shape after bending. The covering part 2b of the conducting wire 2 must be of non-toxic to tissue material, such as Teflon-plastic or similar. In the conducting wire 2 there may be one or several attaching elements (not illustrated), which are possible to be attached to the attaching part. The proportion of the outer diameter of the contact electrode part 1 to the outer diameter of the conducting wire 2 may be 4:1, for example, or such that the former is clearly bigger than the latter. Round the conducting wire 2 against the covering part 2b of it a free-form and free-size attaching part 4 may be connected, which attaching part 4 may be anchored by means of one or several attaching elements in it (FIG. 2A, B) or by means of external attaching elements/material near the subject to be measured. The attachment may be realized on the cranium, for example by means of bolts and hardening cold acrylic, on the skin e.g. by means of a glue sticker 25 (FIG. 2A, B) or a suction cup, or it may be inserted inside tissue in which case the surrounding tissue stabilizes it on place. The material of the attaching part may be wholly or partly flexible and gelatinous substance such as rubber or similar to it material. It may also be of hard material such as glass. The material of the attaching part may reach, in desired extent, round the conducting wire 2 and the contact electrode part 1. For example, half of the ball surface of the contact electrode part 1 may be visible or free from attaching part material.

The outer surface of the attaching part 4 is made of non-toxic to tissue material. There may be an electronic circuitry 24 processing the signal in it. In the attaching part 4 there may be a coupler 3 to be connected to the conducting wire 2, which coupler anchors the conducting wire 2 on place a) by crabbing the covering part 2b of the conducting wire 2 or b) by attaching galvanically to the electroconductive inner part 2a of the conducting wire 2. In the attaching part 4 there may be (not illustrated) an electric coupler for a measuring wire 5 and/or for external (not illustrated) electronic circuitry. The contact electrode part 1 connected to the conducting wire 2 is adjustable to the eye of the test animal 6, for example, by passing the conducting wire 2, in this case, under the upper eyelid inside tissue and conducting it there under skin to a suitable distance where by moving the part of the conducting wire 2 coming outside tissue the contact electrode part 1 may be positioned to the desired point in the eye against the corneal membrane or the conjunctiva (FIG. 3A, B).

In the example in accordance with FIG. 1 the electrode detector is anchored on place by connecting the attaching part 4 outside the skin/tissue to a point, where the conducting wire 2 protrudes from the skin/tissue. The anchoring of the attaching part on the surface of the cranium has been realized by utilizing bolts and hardening acrylic. By employing this technique the construction contact electrode part 1—the conducting wire 2—the attaching part 4, makes a unit in which forces F1-3 and F5-6 keep the ball-like contact electrode part 1 which is monitoring the biopotential permanently placed in desired point in the eye against the conjunctiva or the corneal membrane (FIG. 1). The attaching part 4 limits the movement of the conducting wire 2 in all direction by forces F6 but most of all the longitudinal outward draft F3 of the conducting wire 2 from the attaching part, which is caused by the forces F3 directed to that area of the surface of the contact electrode 1, from the centre of which the conducting wire 2 starts penetrating the tissue through a thin opening which tissue the contact electrode part 1 may not penetrate (FIG. 1). Movements of the contact electrode part 1 are limited by forces F5 directed by the tissue to the conducting wire 2 and which are directed perpendicularly to the direction of the conducting wire 2, on one hand, and by forces F1 and F2 directed by the inner surface of the eyelid and the conjunctiva/corneal membrane of the eye to the contact electrode part 1, on the other hand. As only the attaching part 4 anchors the other end of the conducting wire 2 immovable on place and as the conducting wire 2 is suitably flexible and capable to return after bending back to its shape the contact electrode part 1 does not direct too strong stress on the surface of the eye (FIG. 1) due to the movements of the eye and the eyelid, for example, because it yields. An electrode detector in accordance with above described may be applied in measuring the ERG response of the eye on a test animal 6 (a rat, for example) while it is free to move and conscious, for example, in situation where in chamber 7 visual stimulus refers to diffused light reflected with mirrors 8 and 9 and where a measuring wire 5 connected to the attaching part 4 of the electrode detector transmits the measuring information to the data processing (e.g. computer) unit 12 through an usual signal processing (e.g. amplifier) unit 10 and contact wire 11 (FIG. 1A). By utilizing this technique it is, therefore, possible to evaluate not only the functioning of the eye but also the functioning of the optic nerve on a freely moving test animal while a visual response has been registered from some other point of the visual path, for example from "superior colliculus" structure (FIG. 3).

In accordance with the idea of the invention the ball-like shape of the contact electrode part 1 monitoring biopotential in construction contact electrode 1—the conducting wire 2—the attaching part 4 is such, that it does not cause mechanical irritation changes while placed inside tissue. Secondly, the ball-like contact electrode 1 does not direct too strong stress to the subject to be measured which stress could be caused by movements in the surrounding tissue because it yields under the forces directed to it while being connected to the flexible conducting wire 2 which returns to its shape after bending and the other end of which may be anchored permanently on place in suitable distance from the subject to be measured. Thirdly, the ability to be anchored of the attaching part 4 of the electrode detector by utilizing the attaching elements 25 in it or external attaching element/materials as well as forces (F1-3, F5-6) directed by the surrounding tissue to various sides of the electrode detector cause the ball-like contact electrode part 1 to stay on place. Fourthly, the ability to be anchored of the attaching part excludes the transmission of forces directed from the measuring wire 5 to the contact electrode part 1. Fifthly, the parts of the electrode detector processing the signal, 23 and 24, such as the differential amplifier circuitry, decrease the proportion of interference caused by the movements of the measuring wire 5 and reflected from the surroundings with respect to the biosignal to be measured in wire 5.

Within the frames of the invention solutions and applications differing from the earlier described may be considered. And such the electrode detector may alternatively comprise designs in which the number of ball-like contact electrode parts 1, the attaching parts 4 and conducting wires 2 or the way they are connected to each other is not limited. For example, two contact electrode 1—conducting wire 2 units may be connected to the same attaching part 4, or two contact electrode parts 1 connected one after another to the same conducting wire 2 which has been connected to one attaching part 4. The described electrode detector enables the measurement of visual response (ERG) from the eye on a human, while a ball-like contact electrode part 1 has been inserted under the lower eyelid against the corneal membrane or on the eyelid and the attaching part 4 has been fixed by means of a glue stick or a suction cup on the lower eyelid or on skin near it.

In accordance with the principle which has been described the electrode detector is applicable for measuring a potential change created by whatever biological subject, or of other physical magnitude where the problems connected with the registration are as described.

The invention is not limited to the presented advantageous application but it can vary within the frames of the idea of the invention formed in the claims.

What is claimed is:

1. An electrode detector for monitoring biopotential or other physical magnitude of a tissue of a subject,
    in which the electrode detector comprises a contact electrode part and an attaching part, wherein the contact electrode part and the attaching part are attached to a flexible conducting wire in such a way that the contact electrode part and the attaching part are separate from each other in order to make an effect that the contact electrode part yields, while connected to the flexible conducting wire, although variable forces would be directed to it due to the movement of the tissue thereby reducing the disadvantageous mechanical stress and irritation effects of the contact electrode part on the tissue to be monitored, while the electrode detector is placed against the tissue in such a way that an attaching element or elements of the attaching part keep the electrode detector in place, or while the electrode detector is implanted wholly within the tissue in which case the forces directed to the electrode detector by the surrounding tissue keep the electrode detector in place, and while a voltage signal is conveyed from the contact electrode part to the attaching part through, the conducting wire and while a recorded signal is further transmittable from the attaching part to a signal registering system, which the electrode detector includes;
  a ball-shaped contact electrode part,
  a flexible conducting wire,
  a free-form and free-shaped attaching part,
  electronics coupled to the conducting wire,
  wherein the contact electrode part comprises a covering part which is non-toxic to tissue material and conducts electricity, and an inner part, and
  wherein the conducting wire comprises another covering part which is non-toxic to tissue material and isolates electricity, and another inner part which conducts electricity, and
  wherein the electroconductive covering part of the contact electrode part is galvanically, or capacitively, or indirectly through an electronic circuitry in the contact electrode part itself, connected to the electroconductive inner part of the conducting wire, and
  wherein the attaching part is connected galvanically, or non-galvanically, or indirectly through an electronic circuitry in the attaching part, to the conducting wire, and wherein the attaching part is adapted to be anchored by attaching elements/materials in it or some external attaching elements/materials near the subject to be measured.

2. An electrode detector according to claim 1, in which in the attaching part there is one or more attaching elements.

3. An electrode detector according to claim 1, in which the electronics comprise a differential amplifier inside the attaching part.

4. An electrode detector according to claim 1, in which the electronics comprise a differential amplifier inside the contact electrode part.

5. An electrode detector according to claim 1, in which the attaching part of the electrode detector has been cast into electricity insulating, non-toxic to tissue material.

6. An electrode detector according to claim 1, which comprises one or more contact electrode part, conducting wire and attaching part, which are connectable or which are connected to each other freely.

* * * * *